United States Patent [19]

Vainshtein et al.

[11] 4,144,328
[45] Mar. 13, 1979

[54] N,N,N-TRIMETHYL DERIVATIVES OF POLYENE AMPHOTERIC ANTIBIOTICS, PROCESS OF PRODUCING SAME AND PHARMACEUTICAL COMPOSITION

[76] Inventors: Viktor A. Vainshtein, Suzdalsky prospekt, 28, korpus 1, kv. 64; Valter O. Kulbakh, ulitsa Bukharestskaya, 86, korpus 1, kv. 85; Evgeny D. Etingov, ulitsa Zvezdnaya, 8, kv. 43; Grigory N. Naumchik, Piskarevsky prospekt, 39, kv.20, Piskarevsky prospekt, 39, kv. 20; Oleg N. Ekzemplyarov, Suvorovsky prospekt, 32b, kv. 14; Georgy A. Mikhailets, ulitsa Lanskaya, 10, kv. 100; Grigory E. Grinberg, prospekt Metallistov, 82, kv. 321; Alla N. Egorenkova, kanal Gribcedova, 107/6, kv. 6, all of Leningrad, U.S.S.R.

[21] Appl. No.: 772,471

[22] Filed: Feb. 28, 1977

[51] Int. Cl.² .............................................. A61K 31/71
[52] U.S. Cl. ...................................... 424/180; 536/17
[58] Field of Search ................. 536/4, 9, 17; 424/180

[56] References Cited

U.S. PATENT DOCUMENTS 3,945,993  3/1976  Schaffner et al. .................... 536/17
4,002,741  1/1977  Kulbakh et al. ...................... 536/17

OTHER PUBLICATIONS

Noller, "Chemistry of Organic Compounds", 3rd Ed., 1965, pp. 252-253, W. B. Saunders Co., Phila., Pa.

*Primary Examiner*—Johnnie R. Brown
*Attorney, Agent, or Firm*—Lackenbach, Lilling & Siegel

[57] ABSTRACT

The present invention relates to novel substances; namely, to N,N,N-trimethyl derivatives of polyene amphoteric antibiotics, and to a process of producing same, said substances having the following general formula:

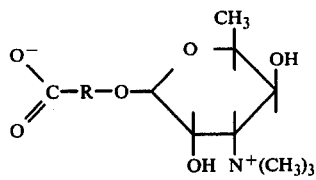

wherein R is aglycone of a polyene amphoteric antibiotic, without the carboxyl group.

The process of producing N,N,N-trimethyl derivatives of polyene amphoteric antibiotics is carried out in an organic solvent medium wherein said polyene amphoteric antibiotics are subjected to complete amino-group methylation by means of a methylating agent with subsequent separation of the end product. N,N,N-trimethyl derivatives of polyene amphoteric antibiotics possess high antibiotic activity thus inhibiting the growth of yeast, yeast-like microorganisms, and filamentous fungi. Said compounds are used in medicine to treat fungal diseases.

10 Claims, No Drawings

N,N,N-TRIMETHYL DERIVATIVES OF POLYENE AMPHOTERIC ANTIBIOTICS, PROCESS OF PRODUCING SAME AND PHARMACEUTICAL COMPOSITION

DETAILED DESCRIPTION OF THE INVENTION

The present invention relates to novel substances, namely, to N,N,N-trimethyl derivatives of polyene amphoteric antibiotics and to a process of producing same.

The herein proposed new compounds possess antifungal effect and are used in medicine for treatment of fungal diseases.

The compounds proposed herein have not been disclosed in any publications.

According to the invention, N,N,N,-trimethyl derivatives of polyene amphoteric antibiotics have the following formula:

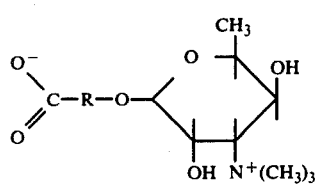

wherein R is aglycone of a polyene amphoteric antiobiotic without the carboxyl group.

The most typical compounds of the group are N,N,N-trimethylamphotericin B, of the formula The ultraviolet spectrum of said compounds coincides with that of the original antibiotics, thus confirming the invariable nature of the conjugated double-bond system in the molecule. The specific absorbtion of purified N,N,N-trimethylamphotericin B at 382 nm is shown to be 1500. The infrared spectrum shows the presence of a fully ionized carboxyl group in the molecule.

The potentiometric titration revealed the presence of a quarternary ammonium group.

N,N,N-trimethyl derivatives of polyene amphoteric antibiotics display antibiotic activity and inhibit the growth of yeast, yeast-like microorganisms, and filamentous fungi.

When tested in vitro by the method of serial dilution in a liquid medium, they exhibit fungistatic effect with respect to the majority of pathogenic fungi at a concentration of 0.31 to 12.5 mg/ml.

The test results for N,N,N-trimethyl derivatives of nystatin and amphotericin B are given below in Table 1.

Table 1

| Microorganism | N,N,N-trimethyl-amphotericin B | N,N,N-trimethyl-nystatin |
|---|---|---|
| Candida albicans | 0.39 | 6.25 |
| Candida tropicalis | 1.5 | 6.30 |
| Cryptococcus neoformans | 3.2 | 1.57 |
| Epidermophyton Kauffman-Wolf | 3.2 | 6.25 |
| Trichophyton gypseum | 3.2 | 12.5 |
| Trichophyton rubrum | 6.3 | 12.5 |
| Pen. granul. | 3.2 | 6.3 |
| Fusorium solani | 3.2 | 6.3 |

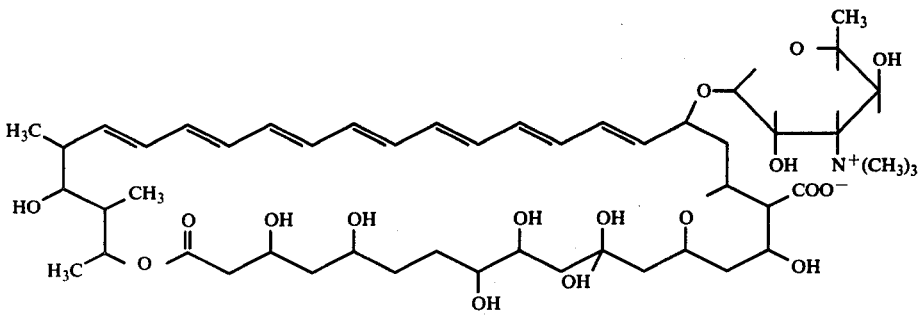

and N,N,N-trimethyl nystatin, of the formula

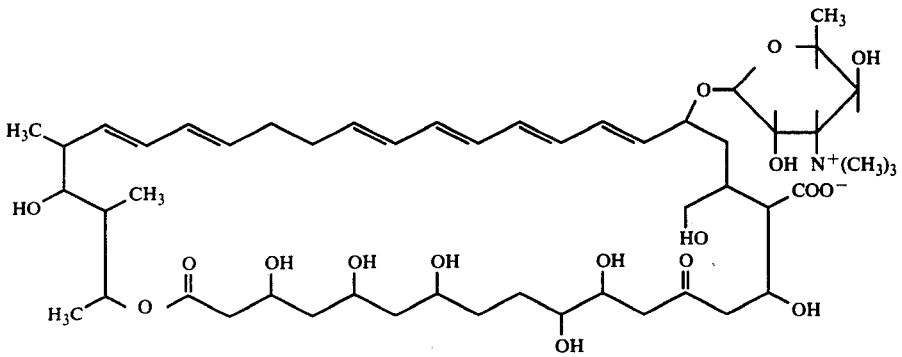

The above-cited compounds are internal salts with a positively charged quarternary amino group and a negatively charged carboxyl groups. They are yellow powders soluble in dimethylformamide, dimethylsulphoxide and in a mixture of dimethylformamide and acetic acid.

N,N,N-trimethylamphotericin B and N,N,N-trimethylnystatin were studied for their acute toxicity on white mice weighing 18-20 g. Water-soluble complexes of the above N,N,N-trimethyl derivatives with polyvinylpyrrolidone were used for said purpose, the active principle concentration being 22–24%. The specimens were dissolved in distilled water and the resulting solution was injected into the caudal vein of the animals.

The test results analysed by the Korber method showed similar toxicity for different batches of N,N,N-trimethylamphotericin B and N,N,N-trimethylnystatin. $LD_{50}$ of said preparations varied from 60.5 to 100 mg/kg, the average value being 80.2 ± 7.0 mg/kg. N,N,N-trimethyl derivatives of amphotericin B and nystatin have shown a toxicity 10–15 times lower than that of original antibiotics with $LD_{50}$ being 7.0 and 11.0 mg/kg, respectively, when used as similar complexes with polyvinylpyrrolidone.

At a dose up to 5 mg/kg to rabbits N,N,N-trimethylamphotericin B resulted in elevation of rectal temperature by 1° C. at most.

A study of chemotherapeutic efficiency of N,N,N-trimethyl derivatives of polyene amphoteric antibiotics was carried out using a model of generalized candidiasis in white mice.

An infective inouculum for the animals was prepared from a 2-day's culture of Candila albicans, which was injected intravenously in a dose of 10–12 million cells per mouse. Low-stock white mice of either sex, weighing 18–20 g, were used in the experiment.

N,N,N-trimethyl derivatives of polyene amphoteric antibiotics in the form of water-soluble complexes with polyvinylpyrrolidone containing 22–24% of the active principle were dissolved in a 5% glucose solution and injected intravenously once every 24 hours. The therapeutic efficiency criterion was based on the survival of the mice of different groups as compared to that infected but not cured. The therapy procedure using N,N,N-trimethyl derivatives of amphotericin B or nystatin consisted of two courses, 4 and 5 days each, with two-day interval therebetween. Alternatively, a continuous seven-day course was used.

All the test animals died in different experiments between the ninth and sixteenth day from the start. 94–100% of the mice treated with 10 or 20 mg/kg of N,N,N-trimethylamphotericin B survived by this time. The minimum test dose (1 mg/kg) ensured survival of 50% of the mice.

The results of treatment of generalized candidiasis in mice using N,N,N-trimethylamphotericin B by an intermittent medication procedure are shown in Table 2.

Table 2

| Number of mice in the group | Dose (mg/kg) | Mice dead in 2 weeks | in 3 weeks | in 4 weeks |
|---|---|---|---|---|
| 16 | 20 | 1 | 1 | 1 |
| 16 | 10 | 0 | 2 | 2 |
| 16 | 5 | 5 | 6 | 7 |
| 16 | 1 | 8 | 9 | 9 |
| 16 | no treatment | 14 | 16 | 16 |

In the case of a continuous treatment procedure, a marked effect of the preparation on the development of experimental infection was noted even at a dose of 0.1–0.2 mg/kg.

The results of treatment of generalized candidiasis in mice using N,N,N-trimethylamphotericin B by a continuous medication procedure are shown in Table 3.

Table 3

| Number of mice in the group | Dose (mg/kg) | Mice dead in 9 days | in 2 weeks | in 3 weeks | in 4 weeks |
|---|---|---|---|---|---|
| 16 | 0.8 | 8 | 8 | 9 | 10 |

Table 3-continued

| Number of mice in the group | Dose (mg/kg) | Mice dead in 9 days | in 2 weeks | in 3 weeks | in 4 weeks |
|---|---|---|---|---|---|
| 31 | 0.4 | 11 | 13 | 15 | 19 |
| 31 | 0.2 | 19 | 22 | 27 | 29 |
| 16 | 0.1 | 10 | 13 | 14 | 15 |
| 16 | 0.05 | 11 | 14 | 15 | 16 |
| 16 | 0.025 | 16 | 16 | 16 | 16 |
| 31 | no treatment | 31 | 31 | 31 | 31 |

In N,N,N-trimethylnystatin treatment, both medication procedures were also used. Depending on the preparation dosage 25–87.5% of the treated mice survived after all the control animals were dead.

The results of treatment of generalized candidiasis in mice with N,N,N-trimethylnystatin by an intermittent medication procedure are shown in Table 4.

Table 4

| Number of mice in the group | Dose (mg/kg) | Mice dead in 2 weeks | in 3 weeks | in 4 weeks |
|---|---|---|---|---|
| 16 | 40 | 2 | 2 | 2 |
| 16 | 20 | 5 | 5 | 5 |
| 16 | 10 | 10 | 10 | 10 |
| 16 | 5 | 10 | 12 | 12 |
| 16 | no treatment | 14 | 16 | 16 |

Similar results were obtained in case of daily administration of the preparation for a period of 7 days.

The results of treatment of generalized candidiasis in mice using N,N,N-trimethylnystatin by a continuous medication procedure are shown in Table 5.

Table 5

| Number of mice in the group | Dose (mg/kg) | Mice dead in 2 weeks | in 3 weeks | in 4 weeks |
|---|---|---|---|---|
| 20 | 10 | 7 | 10 | 13 |
| 19 | 5 | 7 | 10 | 12 |
| 18 | 2.5 | 11 | 14 | 16 |
| 20 | 1.0 | 16 | 18 | 20 |
| 30 | no treatment | 28 | 30 | 30 |

Both preparations showed rather stable results when injected in high doses, since the survival of the animals was practically the same in the course of four weeks of observation.

In accordance with the invention, the process of producing said novel compounds, namely, N,N,N-trimethyl derivatives of polyene amphoteric antibiotics, having the general formula

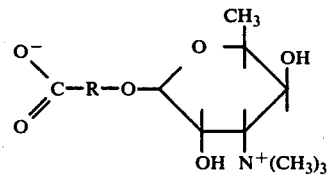

resides in that a polyene amphoteric antibiotic is subjected to complete amino-group methylation by means of a methylating agent, such as methylhalide, methyl sulphate, or methyl ester of organic sulfonic acid. The process is carried out in an organic solvent medium with subsequent isolation of the desired product.

The proposed process is carried out in the following way.

A polyene amphoteric antibiotic is dissolved in an organic solvent, preferably, dimethylsulphoxide or dimethylformamide, which are good solvents for polyene antibiotics, and besides are beneficial for most complete methylation reaction.

A methylating agent selected from the group consisting of halides, methyl sulphates, or methyl esters of organic sulphonic acid, e.g. methyl iodide, dimethylsulphate, methyl ester of paratoluene sulphonic acid, etc. is added with stirring to the resulting solution.

During the methylation process, the amino-group protons are substituted by methyl radicals, whereby a respective acid is liberated. Preferably, the methylation should be performed in the presence of sodium bicarbonate for binding the liberated acid. The sodium bicarbonate weight ratio to the initial antibiotics should lie within 0.5-2.5:1, respectively.

Sodium bicarbonate binds the liberated acid, thus resulting in shift of equilibrium conditions of the reaction towards the formation of the desired product.

The methylation process ends with addition of three methyl radicals to the amino-group nitrogen, the latter becoming positively charged. The compound thus obtained represents an internal salt with a positively charged quarternary atom of nitrogen, and a negatively charged fully ionized carboxyl group.

Methylation is preferably conducted with heating of the reaction mixture to 25-45° C. to minimize the formation of by-products.

The desired product is isolated by precipitating it with water followed by centrifugation, washing, and drying. The yield of the desired product is 70-90 weight percent of theory.

For a better understanding of the present invention, specific examples of the process of producing N,N,N-trimethyl derivatives of polyene amphoteric antibiotics are given hereinbelow by way of illustration.

EXAMPLE 1

1.5 g of amphotericin B having the extinction value $E_{1cm}^{1\%} = 1500$ at 382 nm are loaded into a flask provided with a stirring device. Thereafter, 40 ml of dimethylsulphoxide are added and stirred until amphotericin B is fully dissolved. 0.7 g of sodium bicarbonate are added to the resulting solution, with subsequent addition of a solution containing 1 g of methyl iodide per 10 g of dimethylsulphoxide. The reaction mixture is stirred and kept at 40-45° C. for 1.5-2 hours. Thereafter, the flask is cooled down with subsequent water precipitation of its contents.

The precipitate is centrifugated, washed with water and acetone, and dried in a vacuum drying cabinet, thus giving 1.2 g of the product containing 70% of N,N,N-trimethylamphotericin B.

The UV spectrum of the purified product shows:

Absorption maxima observed at the following wave lengths: $273 \pm 2$ nm; $283 \pm 2$ nm; $345 \pm 2$ nm; $363 \pm 2$ nm; $382 \pm 2$ nm; $406 \pm 2$ nm.

Extinction value at 382 nm is 1500.

IR spectrum: 1720 cm$^{-1}$; 1590 (specifically intensive); 1420 cm$^{-1}$; 1190 cm$^{-1}$; 1080 cm$^{-1}$; 1020 cm$^{-1}$.

Potentiometric titration of 1 g of the purified product:
0.1 N KOH–0.52 ml;
0.1 N HCl–10.1 ml;

Distribution coefficient in the system of methanol-chloroform-borate buffer with pH = 8.27, taken in a ratio of 2:2:1, is 0.82.

EXAMPLE 2

5 g of nystatin having the extinction value of $E_{1cm}^{1\%} = 850$ at 304 nm are loaded into a flask provided with a stirring device. Thereafter, 40 ml of dimethylsulphoxide are added and stirred until the antibiotic is fully dissolved. 13 g of sodium bicarbonate are added to the resulting solution with subsequent addition of a solution containing 6 g of dimethylsulphate per 10 g of dimethylsulphoxide. The reaction mixture is stirred for 1.5 hours at a temperature of 30° C. with subsequent cooling down of the flask, and water precipitation of its contents.

The precipitate is centrifuged, washed with water and acetone, and dried in a vacuum drying cabinet giving 3.7 g of the product containing 68% of N,N,N-trimethylnystatin.

The UV spectrum of the purified product shows:

Absorption maxima observed at the following wavelengths: $292 \pm 2$ nm; $304 \pm 2$ nm; $318 \pm 2$ nm.

The extinction value at 304 nm is 800.

Potentiometric titration of 1 g of the purified product:
0.1 N KOH–0.75 ml;
0.1 N HCl–9.86 ml.

Distribution coefficient in the system of methanol-chloroform-borate buffer at pH = 8.27 (2:2:1) is 1.25.

EXAMPLE 3

5 g of mycoheptin having the extinction value of $E_{1cm}^{1\%} = 1200$ at 382 nm are loaded into a flask provided with a stirring device. Thereafter, 80 ml of dimethylsulphoxide are added and stirred until the antibiotic is fully dissolved. 3.0 g of sodium bicarbonate are added to the resulting solution, with subsequent addition of a solution containing 3.5 g of methyl ester of paratoluene sulphonic acid per 20 ml of dimethylsulphoxide. The reaction mixture is stirred for 1.5 hours at a temperature of 35° C. with subsequent cooling down and separating the product by following the some procedure, as in Example 1.

4.2 g of the product containing 56% of N,N,N-trimethylmycoheptin are obtained.

The UV spectrum of the purified product shows:

Absorption maxima observed at the following wavelengths: $345 \pm 2$ nm; $363 \pm 2$ nm; $382 \pm 2$ nm; $406 \pm 2$ nm.

The extinction value at 382 nm is 1150.

Potentiometric titration of 1 g of the purified product:
0.1 N KOH–0.61 ml;
0.1 N HCl–10.8 ml.

Distribution coefficient in the system disclosed in the preceding Example is 1.1.

EXAMPLE 4

The procedure is the same as in Example 1 except that 5 g amphotericin B are dissolved in 80 ml of dimethylformamide with subsequent addition of 2.8 g of sodium bicarbonate, after which a solution of 4.4 g of methyl iodide in 20 ml of dimethylformamide is poured in. As a result, 4.3 g of the product containing 65% of N,N,N-trimethylamphotericin B are obtained.

The characteristics of the purified product are similar to those described in Example 1.

EXAMPLE 5

The procedure is the same as in Example 2 except that 6 g of dimethylsulphate are substituted for 5 g of methyl iodide. As a result, 4.5 g of the product containing 38% of N,N,N-trimethylnystatin are obtained.

The characteristics of the purified product are similar to those described in Example 2.

EXAMPLE 6

The procedure is the same as in Example 1 except that 5.0 g of amphotericin B are dissolved in 80 ml of dimethylsulphoxide with subsequent addition of 3.0 g of sodium bicarbonate, after which a solution of 5.0 g of methyl iodide in 20 ml of dimethylsulphoxide is poured in. The reaction mixture is stirred up at a room temperature for 2.5 hours. As a result, 4.6 g of the product containing 35% of N,N,N-trimethylamphotericin B are obtained.

The characteristics of the purified product are similar to those described in Example 1.

We claim:

1. N,N,N-trimethyl derivatives of a fungicidal non-aromatic polyene macrolide antibiotic selected from the group consisting of amphotericyn B, mycoheptin, and nystatin heptaenes and tetraenes of the formula:

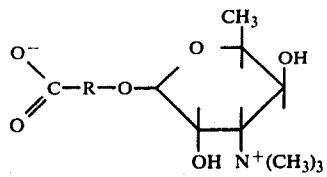

wherein R is aglycone of a fungicidal non-aromatic polyene macrolide antibiotic without the carboxyl group.

2. N,N,N-trimethyl amphotericyn B as the composition of claim 1, having the following formula:

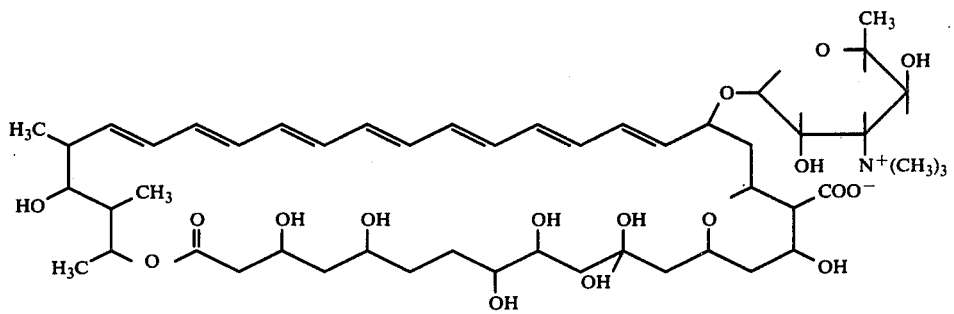

3. N,N,N-trimethyl mycoheptin as the composition of claim 1 having the following formula:

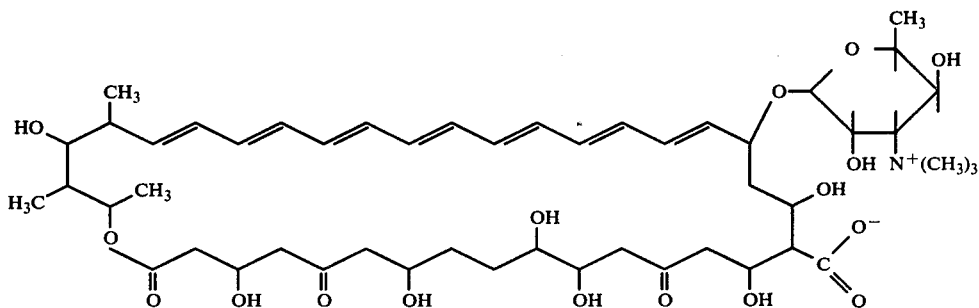

4. N,N,N-trimethyl nystatin as the composition of claim 1 having the following formula:

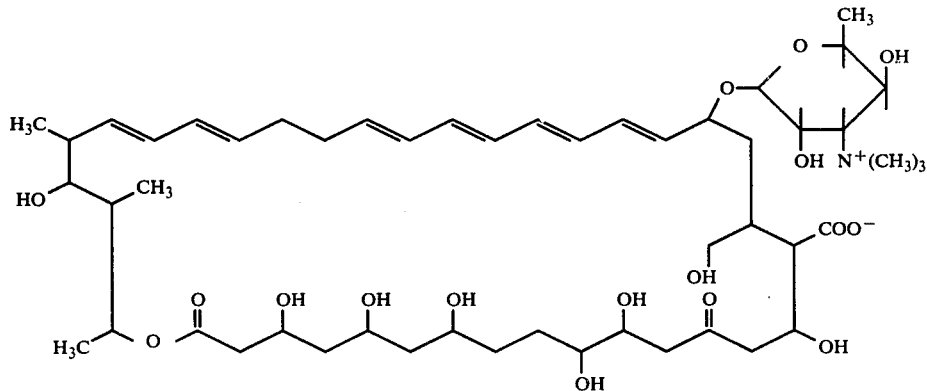

5. A process for preparing N,N,N-trimethyl derivatives of fungicidal non-aromatic polyene macrolide antibiotics selected from the group consisting of amphotericyn B, mycoheptin, and nystatin heptaenes and tetraenes having the formula:

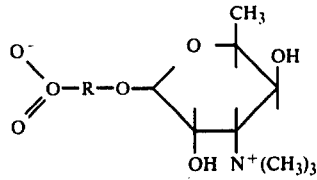

wherein R is aglycone of a fungicidal non-aromatic polyene macrolide antibiotic without the carboxyl group, comprising subjecting said polyene antibiotic macrolide to exhaustive amino sugar-mycosamine methylation in a medium of an organic solvent with a methylating agent selected from the group consisting of methyl halides, methyl sulfates, or methyl esters of organic sulfonic acids; in the presence of sodium bicarbonate followed by isolation of the desired product.

6. The process of claim 5, wherein the methylating agent is selected from the group consisting of methyl iodide, dimethyl sulfate, and methyl esters of toluene sulfonic acids.

7. The process of claim 5, wherein the organic solvent is selected from the group consisting of dimethylsulfoxide and dimethylformamide.

8. The process of claim 5, wherein the amount of sodium bicarbonate varies from 0.5 to 2.5 parts by weight per part by weight of the fungicidal non-aromatic polyene macrolide antibiotic.

9. The process of claim 5, wherein the methylation reaction is conducted at a temperature varying from 25 to 45° C.

10. A medicinal composition comprising as an active ingredient, N,N,N-trimethyl derivatives of a fungicidal non-aromatic polyene macrolide antibiotic selected from the group consisting of amphotericyn B, mycoheptin, and nystatin, heptaenes and tetraenes of the formula:

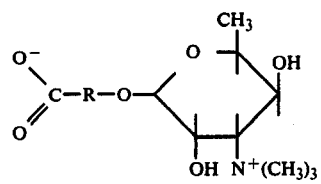

wherein R is aglycone of a fungicidal non-aromatic polyene macrolide antibiotic without the carboxyl group, in combination with a pharmaceutically acceptable carrier.

* * * * *